United States Patent
Rongved et al.

(10) Patent No.: US 7,966,056 B2
(45) Date of Patent: Jun. 21, 2011

(54) MAGNETIC RESONANCE IMAGING METHOD AND COMPOUNDS FOR USE IN THE METHOD

(75) Inventors: Pal Rongved, Nesoddtanken (NO); Jan O. G. Karlsson, Oslo (NO); Karen Briley Saebo, Nesøya (NO)

(73) Assignee: GE Healthcare AS, Oslo (NO)

( * ) Notice: Subject to any disclaimer, the term of this patent is extended or adjusted under 35 U.S.C. 154(b) by 663 days.

(21) Appl. No.: 10/539,175

(22) PCT Filed: Dec. 16, 2003

(86) PCT No.: PCT/NO03/00419
§ 371 (c)(1),
(2), (4) Date: May 10, 2006

(87) PCT Pub. No.: WO2004/054623
PCT Pub. Date: Jul. 1, 2004

(65) Prior Publication Data
US 2006/0235292 A1    Oct. 19, 2006

(30) Foreign Application Priority Data

Dec. 16, 2002  (NO) .................................. 20026027
Jul. 22, 2003  (NO) .................................. 20033312

(51) Int. Cl.
A61B 5/05    (2006.01)
A61B 5/055   (2006.01)
A61B 5/103   (2006.01)

(52) U.S. Cl. ........ 600/420; 600/407; 600/410; 600/411; 600/419; 424/9.3; 424/9.32; 424/9.36

(58) Field of Classification Search .................. 600/410, 600/420–421; 424/9.32, 9.34, 9.36
See application file for complete search history.

(56) References Cited

U.S. PATENT DOCUMENTS

| | | | | |
|---|---|---|---|---|
| 4,647,447 A | * | 3/1987 | Gries et al. | 424/9.36 |
| 4,859,450 A | * | 8/1989 | Goldman | 424/9.34 |
| 4,867,963 A | * | 9/1989 | Maurer et al. | 424/9.36 |
| 4,915,933 A | * | 4/1990 | Matwiyoff | 424/9.34 |
| 4,951,675 A | * | 8/1990 | Groman et al. | 424/9.32 |
| 4,978,763 A | * | 12/1990 | Rocklage et al. | 556/50 |
| 4,980,148 A | * | 12/1990 | Dean | 424/9.364 |
| 5,041,575 A | * | 8/1991 | Gorun et al. | 556/28 |
| 5,099,045 A | * | 3/1992 | Gorun et al. | 556/28 |
| 5,154,179 A | * | 10/1992 | Ratner | 600/420 |
| 5,190,744 A | * | 3/1993 | Rocklage et al. | 424/9.34 |
| 5,217,998 A | * | 6/1993 | Hedlund et al. | 514/575 |
| 5,246,696 A | * | 9/1993 | Dean | 424/9.364 |

(Continued)

FOREIGN PATENT DOCUMENTS
EP          0605908        7/1994

(Continued)

OTHER PUBLICATIONS

Aime, et.al., Reloxametric Evaluation of Novel Manganese (II) Complexes for Application as Contrast Agents in Magnetic Resonance Imaging, J. Biol. Inorg Chem (2002) &: pp. 58-67.

(Continued)

*Primary Examiner* — Unsu Jung (57) ABSTRACT

The present invention relates to a magnetic resonance imaging (MRI) method, in particular to a MRI method enabling early detection of myocardial ischemia and to compounds for use as MR contrast agents in the method.

13 Claims, 2 Drawing Sheets

U.S. PATENT DOCUMENTS

| | | | | |
|---|---|---|---|---|
| 5,268,165 A * | 12/1993 | Hedlund et al. | ............. | 424/9.34 |
| 5,385,719 A * | 1/1995 | Unger et al. | ................. | 528/272 |
| 5,458,127 A * | 10/1995 | Unger et al. | ................. | 600/420 |
| 5,462,053 A * | 10/1995 | Briggs et al. | ................. | 424/9.32 |
| 5,494,655 A * | 2/1996 | Rocklage et al. | ............ | 424/9.36 |
| 5,525,327 A | 6/1996 | Baker et al. | | |
| 5,562,894 A * | 10/1996 | White | ........................ | 424/9.365 |
| 5,650,136 A * | 7/1997 | Platzek et al. | ............... | 424/9.36 |
| 5,672,334 A * | 9/1997 | Ranney | ........................ | 424/9.34 |
| 5,699,801 A * | 12/1997 | Atalar et al. | ................. | 600/410 |
| 5,707,604 A * | 1/1998 | Ranney | ........................ | 424/9.35 |
| 5,744,958 A * | 4/1998 | Werne | ........................ | 324/318 |
| 5,811,076 A * | 9/1998 | Brasch et al. | ............... | 424/9.363 |
| 5,833,947 A * | 11/1998 | Rocklage et al. | ............ | 424/9.36 |
| 5,911,971 A * | 6/1999 | Platzek et al. | ............... | 424/9.363 |
| 5,914,097 A * | 6/1999 | White | ........................ | 424/9.365 |
| 5,980,863 A * | 11/1999 | Harnish et al. | ............... | 424/9.36 |
| 6,054,117 A * | 4/2000 | Platzek et al. | ............... | 424/9.363 |
| 6,106,866 A * | 8/2000 | Ranney | ........................ | 424/499 |
| 6,183,724 B1 * | 2/2001 | Platzek et al. | ............... | 424/9.36 |
| 6,193,950 B1 * | 2/2001 | Platzek et al. | ............... | 424/9.36 |
| 6,312,664 B1 * | 11/2001 | Brasch et al. | ............... | 424/9.35 |
| 6,361,759 B1 * | 3/2002 | Frayne et al. | ............... | 424/9.323 |
| 6,506,972 B1 * | 1/2003 | Wang | ........................ | 174/36 |
| 6,517,814 B2 * | 2/2003 | Liu | ........................ | 424/9.36 |
| 6,553,249 B1 * | 4/2003 | Potthoff | ........................ | 600/420 |
| 6,565,828 B2 * | 5/2003 | Liu | ........................ | 424/1.53 |
| 6,576,222 B2 * | 6/2003 | Platzek et al. | ............... | 424/9.36 |
| 6,673,999 B1 * | 1/2004 | Wang et al. | ........................ | 174/36 |
| 6,713,045 B1 * | 3/2004 | Meade et al. | ............... | 424/9.35 |
| 6,767,360 B1 * | 7/2004 | Alt et al. | ........................ | 623/1.15 |
| 6,770,261 B2 * | 8/2004 | Meade et al. | ............... | 424/9.34 |
| 6,855,309 B2 * | 2/2005 | Platzek et al. | ............... | 424/9.36 |
| 6,906,050 B2 * | 6/2005 | Robinson | ........................ | 514/183 |
| 6,918,927 B2 * | 7/2005 | Bates et al. | ................. | 623/1.15 |
| 7,354,568 B1 * | 4/2008 | Meade et al. | ............... | 424/9.363 |
| 2002/0004032 A1 * | 1/2002 | Liu | ........................ | 424/9.363 |
| 2002/0090341 A1 * | 7/2002 | Watson et al. | ............... | 424/9.36 |
| 2002/0098149 A1 * | 7/2002 | Liu | ........................ | 424/1.65 |
| 2003/0170173 A1 * | 9/2003 | Klaveness et al. | ........... | 424/1.11 |
| 2005/0033407 A1 * | 2/2005 | Weber et al. | ................. | 623/1.15 |

FOREIGN PATENT DOCUMENTS

| | | |
|---|---|---|
| WO | 99/01162 | 1/1999 |
| WO | 01/89584 | 11/2001 |

OTHER PUBLICATIONS

Hu, et.al., "Manganese-enhanced MRI of Mouse Heart During Changes in Inotropy, "Magnetic Resonance in Medicine (2001) 46 pp. 884-890.

Kasten, et.al., Manganese Potentiation of Nitric Oxide-Mediated Vascular Relaxation, European Journal of Pharmacology 253 (1994) pp. 35-43.

Lauterbur, et.al., Augmentation of Tissue Water Proton Spin-Lattice Relaxation Rates by In Vivo Addition of Paramagnetic Ions, Frontiers of Biological Energetics, vol. 1, pp. 752-759.

Marchal, et.al., Paramagnetic Metalloporphyrins: Infarct Avid contrast Agents for Diagnosis of Acute Myocardial Infarction by MRI, Eur. Radiol. 6, (1996) pp. 2-8.

Misselwitz, et.al., "A Toxicologic Risk for Using Manganese Complexes? A Literature Survey of Existing Data Through Several Medical Specialties", Investigative Radiology vol. 30, No. 10, pp. 611-620.

Nagel, et.al., "Cardiovascular Magnetic Resonance: Myocardial Perfusion", Herz, Urban & Vogel 2000, Nr. 4, pp. 409-416.

Prasad, et.al., Preliminary Evaluation of EVP 1001-1: A New Cardiac Specific MR Contrast Agent with Optimal Kinetics for Evaluation of the Ischemic HeartProc. Intl. Soc. Mag. Reson, Med 8 (2000), 1593.

P. Seoane, et.al., Proc. Intl. Soc. Magn. Reson. Med (2000), 1593 and 2047.

Wolf, Role of Magnetic Resonance Contrast Agents in Cardiac Imaging, The American Journal of Cardiology, vol. 66 (1990) pp. 59F-62F.

International Search Report for PCT/NO03/00419 dated May 2004.

International Preliminary Examination Report for PCT/NO03/00419 dated Apr. 2005.

* cited by examiner

MAGNETIC RESONANCE IMAGING METHOD AND COMPOUNDS FOR USE IN THE METHOD

This application is a filing under 35 U.S.C. §371 of international application number PCT/NO2003/000419, filed Dec. 16, 2003, which claims priority to application number 20026027 filed Dec. 16, 2002 and 20033312 filed Jul. 22, 2003, in Norway the entire disclosure of which is hereby incorporated by reference.

The present invention relates to a magnetic resonance imaging (MRI) method, in particular to a MRI method enabling early detection of myocardial ischemia and to compounds for use as MR contrast agents in the method.

Ischemia-related diseases, in particular coronary artery diseases, account for the majority of deaths in the Western countries. Myocardial ischemia is a serious condition and rapid identification and location of myocardial ischemia is therefore highly desirable so that the necessary actions, e.g. therapeutic or surgical treatment, can be taken promptly before irreversible myocardial damage occurs.

Ischemic injury can be considered to result from two main events: (i) hypoxia leading to an inadequate supply of oxygen to the tissues; and (ii) decreased transport of metabolic substrates to the tissues and of metabolic end products from the tissues. Immediate consequences include energy deficit and an accumulation of protons and lactate in the region of ischemia. Other consequences include a marked, potentially harmful stimulation of the sympathetic nervous system, which ultimately leads to a rapid loss of adenosine triphosphate (ATP), an early onset of acidosis and decreased organ function.

Cardiac tissue, like other metabolically active tissues, is particularly vulnerable to ischemic injury. The initial phase of acute myocardial infarction is in general associated with a loss of normal contractile function, which manifests itself as regional dyskinesia. This may be due to an abrupt fall in coronary perfusion pressure, which induces an acute hibernating state, and to the rapid cessation of normal trans-membrane ion transport. Reperfusion of the ischemic myocardium prior to the onset of irreversible injury may lead to a rapid or delayed return (stunning) to normal cardiac metabolism and function.

Magnetic resonance imaging (MRI) has been established as a useful cardiac imaging technique. Although MR techniques using spin-echo imaging are capable of showing the anatomy of the heart, the use of contrast agents is necessary for the detection of myocardial ischemia and infarction. One class of MR contrast agent are paramagnetic contrast agents, which comprise a paramagnetic metal ion, in the form of a salt or in a complex with a chelating/complexing moiety.

The paramagnetic contrast agent GdDTPA (Magnevist™) has been subject of clinical testing for use in myocardial imaging. Although this metal complex has been shown to improve identification of acute myocardial infarcts on MR images in animals and humans, its clinical use in imaging of the myocardium is limited due to its rapid excretion and distribution within the extracellular fluid space.

$Mn^{2+}$ is a paramagnetic metal ion which competes with $Ca^{2+}$ for entry in the contracting myocardium through slow $Ca^{2+}$ channels, resulting in a significant shortening of relaxation time $T_1$ and thus increased signal intensity in normal myocardial tissue. The total influx of $Mn^{2+}$ per time unit is raised during increased heart rate and force of contraction. However, in ischemic myocardium, much less $Mn^{2+}$ is taken up because of reduction in blood flow and decrease in contractility. Hence ischemnic myocardium can be detected and distinguished form normal myocardial tissue by MR imaging using paramagnetic $Mn^{2+}$ as a contrast agent. Further, $Mn^{2+}$ is not a substrate for $Ca^{2+}$ ATPase and the $Na^+/Ca^{2+}$ exchanger during relaxation, and is hence retained in the heart for many hours. This "memory effect" lasts long enough to perform MR investigation in such a way, that a patient administered with a $Mn^{2+}$ comprising contrast agent performs physical exercise outside the MR imager to raise heart rate and subsequent imaging is then performed up to 1 hour after administration. In contrary to $Ca^{2+}$, $Mn^{2+}$ can not induce heart contraction. At high doses, i.e. more than 200 µmol $Mn^{2+}$/kg body weight, $Mn^{2+}$ inhibits $Ca^{2+}$ entry to such an extent, that the force of heart contraction falls. At clinically relevant doses, however, $Mn^{2+}$ has an opposite effect, i.e. it actually increases force of heart contraction (Kasten et al., Eur. J. Pharmacol. 253, 35, 1994) and may show cardiac toxicity. Regarding the target group of patients having to undergo MR imaging to detect myocardial ischemia and infarction, such effects are of course undesirable.

Lauterbur and coworkers investigated $Mn^{2+}$ in the form of manganese chloride ($MnCl_2$) as a contrast agent in animal models (P. Lauterbur et al., Augmentation of tissue water proton spin-lattice relaxation rates by in vivo addition of paramagnetic ions. In: Sutton, Leigh, Scarpa Eds) Frontiers of Biological Energetics Vol I, Academic Press, New York (1978) 752-759). The significant image enhancement of the liver and other organs, but not blood, through the use of manganese chloride was demonstrated. However, the potential clinical utility of manganese chloride was considered to be limited due to its acute cardiac toxicity.

The toxic effects of paramagnetic metal ions are significantly reduced upon complex formation with a chelating agent. This may be viewed as a compromise between relaxivity and toxicity, see V. M. Runge et al., Work in progress: potential oral and intravenous paramagnetic NMR contrast agents. R. B. Lauffer, Paramagnetic Metal Complexes as Water Proton Relaxation Agents for NMR Imaging: Theory and Design. Chem. Rev. 87 (1987) 901-927 found that a thermodynamic formation constant of about $10^{16.5}$ is required to prohibit release of free metal ions from such complexes in vivo.

U.S. Pat. No. 5,246,696 describes manganese or gadolinium complexes such as disodium [[(2-hydroxytrimethylene)dinitrilo]-tetraaceto]manganese (II) and sodium [[(2-hydroxytrimethylene)dinitrilo]-tetraaceto]gadolinium (III) which are said to be useful for enhancing magnetic resonance images of body organs and tissue and having low toxicity. The manganese complex is described to reduce $T_1$ and $T_2$ relaxation times of the kidney, liver, spleen, pancreas and gastrointestinal tract (col. 3, lines 61 to 66). Furthermore, in Example 8 the manganese complex is reported to reduce tissue $T_1$ in particularly the liver but also the heart, pancreas and kidney. However, the document does not disclose that such complexes can be used in the detection of myocardial diseases such as for instance myocardial ischemia.

WO-A-99/01162 describes a method of detecting myocardial ischemia in humans or animals where contrast agents comprising manganese complexes are used together with fast image generation. It is believed that manganese ions are rapidly taken up by viable myocardial cells and retained therein, whereas in reperfused infarcted tissue manganese ions rapidly distribute throughout the tissue but are not retained in non-viable cells. Manganese ions are hence efficiently cleared from this tissue albeit more slowly that from the blood. The imaging is said to be conveniently carried out within a period from 3 to 6 hours post injection. No additional treatment of the patient such as stress treatment is mentioned.

U.S. Pat. No. 5,980,863 describes a formulation containing $Mn^{2+}$ ions in the form of salts, e.g. gluconate salts, and at least 2 times the amount of $Ca^{2+}$ ions. It is noted that Mn ions are toxic; however the formulation of Mn ions with at least two times the molar ratio of Ca ions is held to improve the safety. In the examples, formulations showing a Mn/Ca molar ratio of 1:8-10 are used. A composition believed to be covered by this patent called EVP 1001 is in development.

P. Seoane et al, Proc. Intl. Soc. Magn. Reson. Med 8 (2000) 1593 and 2047 describe a formulation of Mn ions designated EVP 1001 used as a MR contrast agent. Coincident injection of dobutamine, a compound inducing pharmacological stress, was injected in pigs to demonstrate imaging effect and safety of the agent. It is also suggested that stress and contrast agent dosing may be performed outside the magnet.

Although the described contrast agents comprising non-chelated Mn ions and Ca ions appear to have good relaxivity properties, concerns regarding their safety still remain. The administration regime with infusion over a period of several minutes appears important, an accidental bolus injection or too fast infusion rate may lead to acute cardiac toxicity problems.

Calcium salts are not harmless when introduced into the blood circulation. For $CaCl_2$, the $LD_{50}$ on intravenous injection in mice is 42.2 mg/kg. In comparison thereto, for the well known cardiac poison $BaCl_2$, the corresponding $LD_{50}$ dose is 19.2 mg/kg, see I. B. Syed et al., Toxicol. Appl. Pharmacol. 22, (1972), 150. A further disadvantage of using a large amount of calcium in the contrast agent formulation is that calcium competes with manganese for the calcium channels in the entering of the divalent ions into myocytes. This may lead to reduction of efficacy, and a subsequent need to inject higher doses of the contrast agent to compensate for this effect.

Another study of the myocardial memory properties of $MnCl_2$ was reported by Hu et al., Magn. Res. in Medicine 46, (2001), 884-890. A clear contrast effect in MR imaging lasting for about 1 hour could be demonstrated after intravenous infusion of $MnCl_2$ with coincident injection of the pharmacological stress agent dobutamine. The safety risk related to use of the highly water-soluble agent $MnCl_2$ as mentioned above is still a concern even when administering $MnCl_2$ with a slow infusion rate.

Thus, the use of injections or infusions of non-chelated $Mn^{2+}$, especially as a concentrated bolus, holds the risk of cardiac toxicity, particularly for patients having impaired myocardial function. $Mn^{2+}$ is taken up into cells in the healthy part of the myocardium and may thus impart the function of the unaffected part of the diseased heart.

Consequently, the use of free manganese ions and other paramagnetic metal ions such as gadolinium ions in the body is limited by their toxicity. Thus, complexing of these cations with suitable ligands and chelates is recommended, because it serves to greatly reduce their toxicity whilst partly retaining their paramagnetic properties.

However, if the thermodynamic formation constant of such complexes is high, no detectable amount of free metal ion is released rapidly enough in vivo, and the contrast agent will not be taken up by the cells of the viable tissues. Commercially available extra cellular contrast agents such as Magnevist™ and Dotarem™ are examples of contrast agents with high stability constants and are hence not favourable contrast agent for the detection of myocardial ischemia.

The use of physical and/or pharmacological stress increases the contrast difference between normal and ischemic myocardium by 4-5 times. It is therefore favourable to use a regime of stress as it allows for lower doses of the contrast agent. Further, a method that allows the contrast agent to be administered before the patient is placed inside the MR magnet would be a preferred procedure in the clinical situation.

It is therefore a need for a contrast agent comprising a contrast generating moiety (e.g. a paramagnetic metal ion) that is taken up by viable myocytes in a sufficient amount to provide a sustained contrast effect in the state of art imaging protocol. The contrast generating moiety must remain inside the myocytes for a period of time sufficiently long to allow the patient to undergo the MR examination procedure, i.e. it must have a "memory effect". Further, the difference in contrast enhancement between the blood pool, the ischemic myocardial tissue and the normal myocardial tissue must be sufficient to provide delineation between the ischemic and the normal myocardial tissue. The contrast agent must have a safety profile that avoids the disadvantages described above for free metal ions, e.g. non-chelated manganese ions like manganese salts.

It has surprisingly now been found that contrast agents that can provide intermediate release of paramagnetic metal ions (the contrast generating moiety)—like $Mn^{2+}$ from complexes of the metal ion and a complexing/chelating moiety—after intravenous injection are especially useful in diagnosis of cardiac diseases. Such contrast agents provide an optimal compromise between sufficient efficacy and safety. The contrast agents preferably have a "memory effect", meaning that contrast generating moiety of the contrast agent transiently accumulates in the cells of the myocardium providing contrast difference between normal tissue and diseased tissue. In the imaging window, the contrast in blood pool is not significantly different from baseline blood pool pre-contrast. Further, no cardiotoxicity measured as significant changes in the physiological parameters in the blood are observed during the imaging procedure.

The contrast agents having a "memory effect" allow exposing the human or non-human body to physical and/or pharmacological stress. Contrast agents according to the invention comprise relatively weak complexes where controlled amounts of the paramagnetic ions are released into the blood after administration. The released paramagnetic metal ions are able to enter the viable cells in the regions of interest, e.g. the myocardium, and remain in the cells during the time of image data acquisition. The concentration of the paramagnetic ions must be sufficient to provide a $T_1$ shorting in the imaged area, but must not exceed the level where cardiotoxicity becomes a problem. The body under examination is preferably exposed to stress before the contrast agent is administered; most preferably the contrast agent is administered at peak stress and before the patient is placed in the MR machine.

Thus, viewed from one aspect the invention provides a method of MR imaging comprising
a) administering a contrast agent comprising at least one complex comprising a paramagnetic metal ion and a complexing moiety to a human or non-human animal body wherein said complex has a thermodynamic formation constant between $10^3$ and $10^{16}$;
b) exposing said body to a regime of physical and/or pharmacological stress before or simultaneously to the contrast agent administration;
c) collecting MR imaging data and;
d) optionally providing MR images of an area of interest.

The contrast agent comprises either one single complex or a mixture of complexes as described in the preceding paragraph.

Viewed from another aspect the present invention provides compounds of the formula (I)

$$Mn_m(P_3O_{10}{}^{5-})_nZ_o \qquad (I)$$

where m, n and o are positive integers from 1 and 10 and Z is hydrogen or a pharmaceutical acceptable counterion for use in a MR contrast agent. Suitable pharmaceutical acceptable counterions are for instance ammonium, substituted ammonium, alkali metal or alkaline earth metal (e.g. calcium) cations or anions deriving from an inorganic or organic acid. In a preferred embodiment, Mn is $Mn^{2+}$.

Viewed from a further aspect the present invention provides use of compounds of the formula (II)

$$Mn_m HPTA\ Z_o \qquad (II)$$

where m is 1 or 2, o is 0 to 2 and Z is hydrogen or a pharmaceutical acceptable counterion for the manufacture of a contrast agent for use as a MR contrast agent in the detection of myocardial ischemia. The IUPAC nomenclature of HPTA is 1,7-dicarboxy-2,6-bis(carboxymethyl)-4-hydroxy-2,6-diaza)-heptane. In a preferred embodiment, Mn is $Mn^{2+}$. Suitable pharmaceutical acceptable counterions are for instance ammonium, substituted ammonium, alkali metal or alkaline earth metal (e.g. calcium) cations or anions deriving from an inorganic or organic acid.

The compounds of formulas (I) and (II) illustrates preferred examples of the complex used in the method according to the invention.

Further aspects of the invention will be evident from the claims and the specification.

From a first aspect, the invention provides a method of MR imaging comprising
e) administering a contrast agent comprising at least one complex comprising a paramagnetic metal ion and a complexing moiety to a human or non-human animal body wherein said complex has a thermodynamic formation constant between $10^3$ and $10^{16}$;
f) exposing said body to a regime of physical and/or pharmacological stress before or simultaneously to the contrast agent administration;
g) collecting MR imaging data and;
h) optionally providing MR images of an area of interest.

In a preferred embodiment, the method of imaging is used to identify areas suffering from myocardial ischemia, hence the area of interest is the myocardium.

In the method of MR imaging according to the invention it is important that the paramagnetic metal ions from the complex are released in a controlled manner. The release of a metal ion from complex is related to the stability constant of the complex. It was found that a complex having a thermodynamic formation constant k between $10^3$ and $10^{16}$ (log k between 3 and 16) provides a sufficiently rapid release of the paramagnetic metal ion to provide an intracellular concentration of said metal ion in the myocardium that is adequate to generate myocardial contrast in magnetic resonance imaging. In such complexes, the release rate is sufficiently retarded to avoid intracellular myocardial accumulation of metal ions in a concentration risking adverse events in the body after intravenous injections such as bolus injections. Preferably, the thermodynamic formation constant k is between $10^5$ and $10^{10}$ (log k between 5 and 10), more preferably between $10^7$ and $10^{9.5}$ (log k between 7 and 9.5).

The complex used in the method of the invention may be in the form of an ionic or non-ionic complex. Suitable paramagnetic metal ions are any paramagnetic metal ions that are taken up by intact cells or that are able to pass cell membranes of intact cells. Preferred paramagnetic metal ions are those which are taken up by the Ca channels in myocardial cells, particularly preferred are Mn ions, more particularly preferred $Mn^{2+}$.

Preferred complexing moieties in the complexes used in the method of the invention are low molecular weight hydrophilic complexing moieties. Examples of useful complexing agents are N,N'-bis-(pyridoxal-5-phosphate)ethylenediamine-N,N'-diacetic acid (DPDP), N,N'-bis-pyridoxal-ethylenediamine-N,N'-diacetic acid (PLED), diethylenetramine-pentaacetic acid-bismethylamide (DTPABMA), ethylenediamine-tetraacetic acid-bismethylamide (EDTAB-MA)polyphosphates, and in particular triphosphate ($P_3O_{10}{}^{5-}$; TPP)) and 1,7-dicarboxy-2,6-bis(carboxymethyl)-4-hydroxy-2,6-diaza)-heptane (HPTA).

A preferred complex for use in the method of the invention is MnDPDP, which has a thermodynamic formation constant of $10^{15.1}$.

Further preferred complexes for use in the method of the invention are the complexes of formula (I)

$$Mn_m(P_3O_{10}{}^{5-})_nZ_o \qquad (I)$$

where m, n and o are positive integers from 1 and 10 and Z is hydrogen or a pharmaceutical acceptable counterion for use in a MR contrast agent. Suitable pharmaceutical acceptable counterions are for instance ammonium, substituted ammonium, alkali metal or alkaline earth metal (e.g. calcium) cations or anions deriving from an inorganic or organic acid. In a preferred embodiment, Mn is $Mn^{2+}$. A further preferred embodiment the complexes of formula (I) is manganese triphosphate (denoted MnTPP) of the formula (III)

$$Mn^{2+}(P_3O_{10}{}^{5-}) \qquad (III)$$

MnTPP has a thermodynamic formation constant of $10^{7.1}$ (Smith & Martell, Critical Stability Constants, Vol. 4, Inorganic Complexes, Plenum Press, New York (1976) page 63) and is found to provide a particularly suitable in vivo release rate of manganese.

Other complexes that are particularly useful in the method of the invention are complexes of the formula (II)

$$Mn_m HPTA\ Z_o \qquad (II)$$

where m is 1 or 2, o is 0 to 2 and Z is hydrogen or a pharmaceutical acceptable counterion. Suitable pharmaceutical acceptable counterions are for instance ammonium, substituted ammonium, alkali metal or alkaline earth metal (e.g. calcium) cations or anions deriving from an inorganic or organic acid. In a preferred embodiment, Mn is $Mn^{2+}$.

More preferred complexes of the formula (II) are $$Mn\ Na_2\ HPTA\ (IV)\ and\ Mn_2\ HPTA \qquad (V)$$

wherein Mn is preferably $Mn^{2+}$. The complex of formula (IV) has a thermodynamic formation constant k of $10^{9.1}$.

Where the complex used in the method of the invention carries an overall charge, it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine, calcium and sodium salts are particularly preferred.

In a further preferred embodiment, the complex used in the method of the invention comprises $Mn^{2+}$ and a complexing moiety, said complex showing a dissociation of greater than 50% and a half-life of less than 1 min under physiologic conditions. As explained before, it is important for the efficacy of the contrast agent that the paramagnetic metal ion, preferably $Mn^{2+}$, is released from the complex fast enough that a relatively high concentration of free $Mn^{2+}$ is present, which can enter the myocytes. On the other hand, the concentration of free $Mn^{2+}$ should not be such that there is a risk of acute cardiac toxicity. It has now been found that complexes showing a dissociation of greater than 50% under physiologic conditions and a half-life of less than 1 min are preferred as they fulfil these criteria. A dissociation of greater than 50% under physiologic conditions ensures a concentration of free $Mn^{2+}$ that is high enough to provide good efficacy. However, it is further favourable that $Mn^{2+}$ is released quickly from the complex, hence the complexes preferably used in the method of the invention have a half-life of less than 1 min under physiologic conditions.

In a preferred embodiment, the complexes show a dissociation of greater than 60% under physiologic conditions, more preferably a dissociation of greater than 70% and most preferably a dissociation of greater than 80%.

The term "physiologic conditions" in the context of the application means in the presence of blood plasma, preferably mammalian or human blood plasma, at a temperature range of 35 to 40° C. Blood plasma contains a variety of endogenous cations like for instance $Zn^{2+}$, $Fe^{2+}$, $Cu^{2+}$ or $Mg^{2+}$. In the presence of these cations, transmetallation occurs, meaning that $Mn^{2+}$ is released from the complex and the complexing moiety subsequently forms complexes with these endogenous cations, when the selectivity of the complexing moiety is greater for specific endogenous cations than for $Mn^{2+}$.

There are several possible methods to determine % dissociation and half-life of the complexes used in the method of the invention under physiologic conditions. Generally, methods to observe and determine dissociation kinetics are known in the art, for instance, various spectroscopic method can be used. In one embodiment, a sample of the complex is mixed with blood plasma and the dissociation kinetics are followed by HPLC. % dissociation and half-life of the complex are be calculated from the HPLC data in a way known in the art.

In a preferred embodiment, % dissociation and half-life of the complexes are determined by MR spectroscopy. The complex is mixed with blood plasma of a temperature between 35 to 40° C. (=sample) and the longitudinal relaxation rates, R1, of the sample are determined over a certain time interval at this temperature. The longitudinal relaxivity, $r_1$, of the sample is determined as a function of time according to equitation (1)

$$r_1 = (R1_{sample} - R1_{blank})/\text{concentration } Mn^{2+}[mM] \quad (1)$$

wherein $r_1$ is the longitudinal relaxivity ($s^{-1}$ $mM^{-1}$), $R1_{sample}$ is the relaxation rate of the sample, i.e. the complex in plasma ($s^{-1}$) and $R1_{blank}$ is the relaxation rate of the plasma without the complex ($s^{-1}$). Preferably, a $Mn^{2+}$ concentration of about 0.05 to 0.2 mM is used as a linear relationship exists between R1 and the $Mn^{2+}$ concentration in plasma for this concentration range. % dissociation in plasma is determined according to equitation (2)

$$\% \text{ dissociated} = (1 - (r_{1MnCl2 \text{ in plasma}} - r_{1sample, t})/r_{1MnCl2 \text{ in plasma}}) \cdot 100 \quad (2)$$

wherein $r_{1MnCl2 \text{ in plasma}}$ is the relaxivity of $MnCl_2$ in plasma and $r_{1sample, t}$ is the relaxivity of the sample at a given time t.

Preferably, the time interval is about 1 hour, hence % dissociation is calculated after 1 hour incubation of the complex in plasma at a temperature in the range of 35 to 40° C. The $r_1$ values as a function over time, for instance over a 1 hour time interval, are used to calculate the rate of dissociation and the half-life ($t_{1/2}$) of the complex in plasma at the given temperature.

The complexes used in the method of the invention can be produced from commercially available complexing moieties or from complexing moieties described in the literature and oxides or acid salts such as chlorine and acetate salts of the paramagnetic metal for example as described in U.S. Pat. No. 4,647,447. The synthesis of MnDPDP is described in EP 0290047 B1. The synthesis of HPTA-complexes is described in U.S. Pat. No. 5,246,696. These documents are hereby included by reference. Briefly, the formation of the Mn complexes for use in the method of the invention involves dissolving or suspending manganese oxide or manganese salts like manganese chloride or manganese acetate in water or a lower alcohol like methanol, ethanol or isopropanol. To this solution or suspension is added an equimolar amount of the complexing moiety in water or a lower alcohol and the mixture is stirred, if necessary with heating, until the reaction is completed. If the complex formed is insoluble in the solvent used, the reaction product is conveniently isolated by filtering. If it is soluble, the reaction product is isolated by evaporating to dryness, e.g. by spray drying or lyophilising.

In a preferred embodiment, the aforementioned Mn complexes used in the method of the invention comprise Mn in the form of $Mn^{2+}$ as this ensures most effective uptake by the calcium channels in the myocytes. When these complexes are used in the MR contrast agents used in the method of the invention, the contrast agent formulation preferably comprises an antioxidant e.g. ascorbic acid or a reducing sugar to inhibit oxidation to $Mn^{3+}$ and $Mn^{4+}$ with subsequent precipitation of $MnO_2$. Providing the commercial contrast agent product in lyophilized form in an inert gas atmosphere, e.g. argon gas atmosphere, will stabilise the product during storage.

In a further preferred embodiment, the complexes used in the method according to the invention comprise $Mn^{2+}$ and a complexing moiety and further 0 to 2 mol $Ca^{2+}$ per mol $Mn^{2+}$, preferably 0.1 to 2 mol, more preferably 0.1 to 1.75 mol and most preferably 0.5 to 1 mol. Hence, a particularly preferred complex is CaMnHPTA containing 1 mol $Ca^{2+}$ per mol $Mn^{2+}$ and the preferred complexing moiety HPTA. Another particularly preferred contrast agent comprises $Z_2$MnHPTA, wherein Z is hydrogen or an alkali metal ion, preferably a sodium ion, and $Ca^{2+}$ with 0.5 mol $Ca^{2+}$ per mol $Mn^{2+}$. In a preferred embodiment, the complexes used in the inventive method are prepared from a mixture of $Ca^{2+}$ (e.g. in the form of a salt like calcium chloride) and $Mn^{2+}$ in the described molar ratio. In another preferred embodiment, the contrast agent is prepared by adding $Ca^{2+}$ (e.g. in the form of a salt like calcium chloride) to a $Mn^{2+}$ containing complex to obtain the described molar ratio.

For use in the method of the invention, the contrast agents comprising the complexes may further comprise conventional pharmaceutical or veterinary formulation aids, for example stabilisers, antioxidants, osmolality adjusting agents, buffers and pH adjusting agents. The contrast agents may be in a form suitable for injection or infusion directly or after dispersion in or dilution with a physiologically acceptable carrier medium, e.g. water for injections. Thus the contrast agents may be in a conventional pharmaceutical administration form such as a lyophilised product, a powder, a solution, a suspension, a dispersion, etc. However, solutions in physiologically acceptable carrier media will generally be preferred. Suitable additives include, for example, physiologically biocompatible buffers.

Solutions of the contrast agent for parenteral administration, e.g. intravenous administration, should be sterile and free from physiologically unacceptable agents, and should have low osmolality to minimize irritation or other adverse effects upon administration. The contrast agent solutions should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions. Such vehicles are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975).

Solutions of the contrast agent may further contain preservatives, antimicrobial agents, buffers and antioxidants conventionally used for parenteral solutions. Excipients and other additives which are compatible with the complexes and which will not interfere with the manufacture, storage or use of the products may also be employed.

Preferably, the contrast agents used in the method of the invention comprising the complexes are administered at a dose of 0.1 to 30 µmol paramagnetic metal ion/kg body weight, more preferably 0.5 to 30 µmol paramagnetic metal ion/kg, most preferably 10 to 20 µmol paramagnetic metal ion/kg.

In the method according to the invention the contrast agent is preferably administered in a bolus injection although slow injection or infusion of the contrast agent is also suitable. For $Mn^{2+}$ complexes with low formation constants, e.g. in the area $10^3$ to $10^8$ there might be a risk that the release of $Mn^{2+}$ from the complex may still be sufficiently rapid to induce cardiotoxic reactions in the body. To avoid such toxic reactions, the contrast agent comprising such complexes could be provided in solutions comprising low concentrations of such complexes. If it is preferred to provide the contrast agent in dry form, e.g. as a lyophilized powder, for on site preparation of the solution for injection, complexes with properties that avoid the preparation of high concentration solutions provide an additional advantage. For example the sodium salt of MnTPP, $Na_3MP_3O_{10}$, has a limited solubility, thus prohibiting injections of highly concentrated solutions of manganese. The maximum solubility of the sodium salt of MnTPP in water is 23 mmol/L, which is close to a suitable formulation for injection at a concentration of 15 mmol/L. At a clinical dose of 10 µmol/kg, a volume of more than 45 ml of contrast agent solution needs to be injected. This injection volume additionally prohibits rapid bolus injections of sodium salts of MnTPP.

According to the method of the invention, the body is exposed to a regime of stress.

Said stress is preferably a physical stress outside the magnet, e.g. exercise stress for example on a treadmill. Alternatively, pharmacological stress may be employed e.g. by the administration of agents like dobutamine or dipyridamole. The contrast agent can be administered to the body during or after stress exposure. Preferably, the contrast agent is administered at peak stress. The use of physical or pharmacological stress increases blood flow significantly (4-5 times) which in turn leads to significant contrast difference between normal and ischemic myocardium. Further, a method that allows the contrast agent to be administered before the patient is placed in side the MR magnet is a preferred procedure in the clinical situation.

Preferably the body is subjected to MR imaging after a time period sufficient for the MR signal intensity of the blood pool to become insignificantly different from the precontrast baseline signal intensity. More preferably, the body is subjected to MR imaging after a time period of at least 5 minutes from the admninistration of the contrast agent, more preferably within a period of 10 to 60 minutes, even more preferably within a period of 10 to 45 minutes and most preferably within a period of 15 to 30 minutes after contrast agent administration.

Highly $T_1$-sensitive, fast or ultra-fast imaging techniques which enable the generation of a series of images with a time interval as short as possible between successive images are preferred. This will ensure the acquisition of data during the first passage of the contrast agent through the heart, thus enabling a clinically acceptable dose of contrast agent to be used. MR imaging techniques capable of generating images with time intervals of less than 100 milliseconds are particularly preferred. Thus MR imaging techniques suitable in the method of the invention include gradient echo and echo planar imaging, especially inversion recovery echo planar imaging, e.g. gradient refocused inversion recovery echo planar imaging. Particularly suitable echo planar imaging techniques are those in which TI (inversion time) is 100 to 800 milliseconds, TR (repetition time) corresponds to the heart rate and TE (echo time) is less than 20 milliseconds, e.g. 10-20 milliseconds. The sensitivity of the imaging technique may be increased by gating to every heartbeat. Flip angles for use in the preparation interval preceding image data acquisition may either be 180° or 90°, with 90° being preferred. Using a flip angle of 90° it is preferable to acquire single heart beat temporal resolution.

The method of the invention is preferably used to detect and identify myocardial ischemia or myocardial infarction.

In a further aspect, the invention provides compounds of the formula (I)

$$Mn_m(P_3O_{10}^{5-})_n Z_o \qquad (I)$$

where m, n and o are positive integers from 1 and 10 and Z is hydrogen or a pharmaceutical acceptable counterion for use in a MR contrast agent. Suitable pharmaceutical acceptable counterions are for instance ammonium, substituted ammonium, alkali metal or alkaline earth metal (e.g. calcium) cations or anions deriving from an inorganic or organic acid. In a preferred embodiment, Mn is $Mn^{2+}$.

A preferred embodiment of formula (I) is the manganese triphosphate (MnTPP) complex of the formula (III)

$$Mn^{2+}(P_3O_{10}^{5-}) \qquad (III)$$

particularly preferred in the form of a pharmaceutical acceptable salt such as its sodium salt $Na_3MnP_3O_{10}$.

The synthesis of manganese triphosphate complexes of the formula (I) may be carried out as described in Example 1b) of the present application. Briefly, manganese chloride $MnCl_2$ is reacted with a triphosphate such as pentasodiumtriphosphate preferably in the presence of an antioxidant to prevent oxidation of $Mn^{2+}$.

Viewed from a further aspect the present invention provides use of compounds of the formula (II)

$$Mn_m HPTA\, Z_o \qquad (II)$$

where m is 1 or 2, o is 0 to 2 and Z is hydrogen or a pharmaceutical acceptable counterion for the manufacture of a contrast agent for use as a MR contrast agent in the detection of myocardial ischemia. The IUPAC nomenclature of HPTA is

1,7-dicarboxy-2,6-bis(carboxymethyl)-4-hydroxy-2,6-diaza)-heptane. In a preferred embodiment, Mn is $Mn^{2+}$. Suitable pharmaceutical acceptable counterions are for instance ammonium, substituted ammonium, alkali metal or alkaline earth metal (e.g. calcium) cations or anions deriving from an inorganic or organic acid. In a preferred embodiment, Z is Na.

Particularly preferred complexes of the formula (II) are

Mn Na$_2$ HPTA (IV)

and

Mn$_2$ HPTA (V)

wherein Mn is preferably $Mn^{2+}$.

The complexes of the formula (II) may be synthesised according to the methods disclosed in U.S. Pat. No. 5,246,696.

In a preferred embodiment, the aforementioned Mn complexes comprise Mn in the form of $Mn^{2+}$ as this ensures most effective uptake by the calcium channels in the myocytes. When these complexes are used in MR contrast agents, the contrast agent formulation preferably comprises an antioxidant e.g. ascorbic acid or a reducing sugar to inhibit oxidation to $Mn^{3+}$ and $Mn^{4+}$ with subsequent precipitation of $MnO_2$. Providing the commercial contrast agent product in lyophilized form in an inert gas atmosphere, e.g. argon gas atmosphere, will stabilise the product during storage.

For MR imaging, the aforementioned Mn complexes are preferably administered at a dose of 0.1 to 30 μmol Mn/kg body weight, more preferably 0.5 to 30 μmol Mn/kg, most preferably 10 to 20 μmol Mn/kg.

Another aspect of the invention is the use of a mixture comprising a complex comprising $Mn^{2+}$ and a complexing moiety, wherein said complex shows a dissociation of greater than 50% and a half-life of less than 1 min under physiologic conditions and 0.1 to 2 mol $Ca^{2+}$ per mol $Mn^{2+}$ for the manufacture of a contrast agent for use in MR imaging of the myocardium, preferably for use in the MR imaging detection of myocardial ischemia and infarction.

A preferred embodiment is the use of a mixture comprising a complex having a thermodynamic formation constant between $10^3$ and $10^{16}$ which comprises $Mn^{2+}$ and a complexing moiety, wherein said complex shows a dissociation of greater than 50% and a half-life of less than 1 min under physiologic conditions and 0.5 to 1 mol $Ca^{2+}$ per mol $Mn^{2+}$ for the manufacture of a contrast agent for use in MR imaging of the myocardium, preferably for use in the MR imaging detection of myocardial ischemia and infarction.

A more preferred embodiment is the use of a mixture comprising a complex having a thermodynamic formation constant between $10^3$ and $10^{16}$ which comprises $Mn^{2+}$, HPTA and 0.1 to 2 mol $Ca^{2+}$ per mol $Mn^{2+}$ for the manufacture of a contrast agent for use in the MR imaging of the myocardium, preferably for use in the MR imaging detection of myocardial ischemia and infarction.

An even more preferred embodiment is the use of a mixture comprising a complex having a thermodynamic formation constant between $10^3$ and $10^{16}$ which comprises $Mn^{2+}$, HPTA and 0.5 to 1 mol $Ca^{2+}$ per mol $Mn^{2+}$ for the manufacture of a contrast agent for use in the MR imaging of the myocardium, preferably for use in the MR imaging detection of myocardial ischemia and infarction.

The following non-limiting examples illustrate features of the invention. R1 denotes the longitudinal relaxivity rate in $s^{-1}$

EXAMPLES

Example 1

Preparation of Manganese Complexes a) Preparation of 15 mM $MnCl_2$ (Comparison Example)

7.4 g (37.5 mmol) manganese chloride tetrahydrate ($MnCl_2.4H_2O$) and 13.2 g (75 mmol) ascorbic acid were dissolved in 2.5 L of purified water to give a $M^{2+}$—concentration of 15 mM. The solution was filtrated through 0.22 μm filter prior to injection.

b) MnDPDP

MnDPDP is commercially available under the name Teslascan™ from Amersham Health AS, Norway.

c) Preparation of 15 mM Manganese Triphosphate Solution 7.4 g (37.5 mmol) manganese chloride tetrahydrate ($MnCl_2.4H_2O$), 27.6 g (75 mmol) penta-sodium triphosphate and 13.2 g (75 mmol) ascorbic acid were dissolved in 2.5 L of purified water to give a $Mn^{2+}$—concentration of 15 mM. The solution was filtrated through 0.22 μm filter prior to injection.

Example 2

Relaxation Rate Studies in Pig

Figure 1:
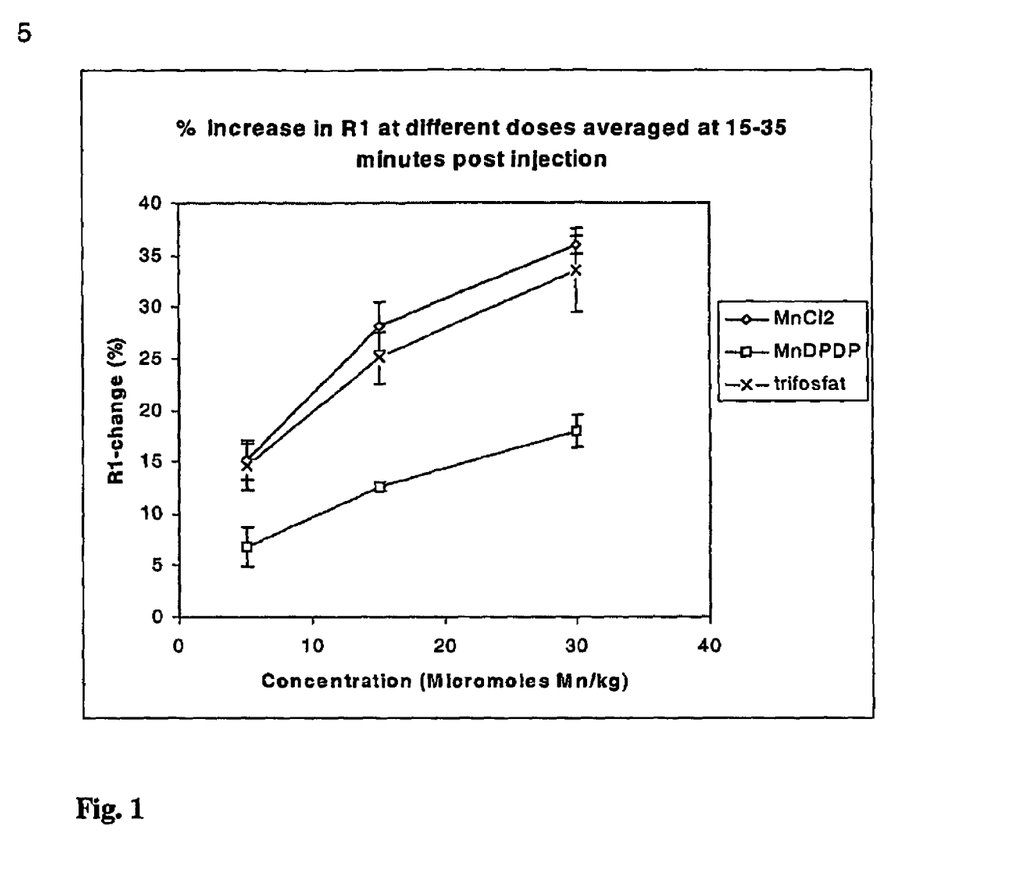
FIG. 1 is a plot of R1 percent change as a function of $MnCl_2$, MnTPP and MnDPDP concentrations in micromoles of Mn per kilogram of body weight.

An ischemia pig model was established by introduction of a tubing with known inner (0.5 mm) and outer (1.75 mm) diameter and a length of 6 mm inserted into LAD (left ascending coronary artery) with catheter comprising a guiding wire. After introduction of the tubing into the artery, the catheter and the guiding wire were removed. To verify that the coronary artery was open pre and post injection of the contrast agent, X-ray angioography was performed, see FIG. 3. Three ischemic pigs of 20-30 kg body weight were given cumulative doses of the following contrast agents: 5, 15 and 30 μmol/kg of $MnCl_2$, MnTPP and MnDPDP. R1 was measured in blood and myocardium at 5, 15, 25 and 35 minutes after injection. The result is shown in FIG. 1.

Example 3

Imaging

In an anaesthesed pig, heart rate and systolic/diastolic blood pressure were monitored.

Dobutamine was infused at a dose of 10 μg/kg body weight/min and increased by 10 μg/kg/min every second minute until a PRP (pressure-rate product) of a factor 2.5 was achieved.

10 μmol/kg body weight of MnTPP was injected in a bolus during 4 seconds. No clinical signs represented by changes in physiological parameters were observed during the experiment.

Figure 2:
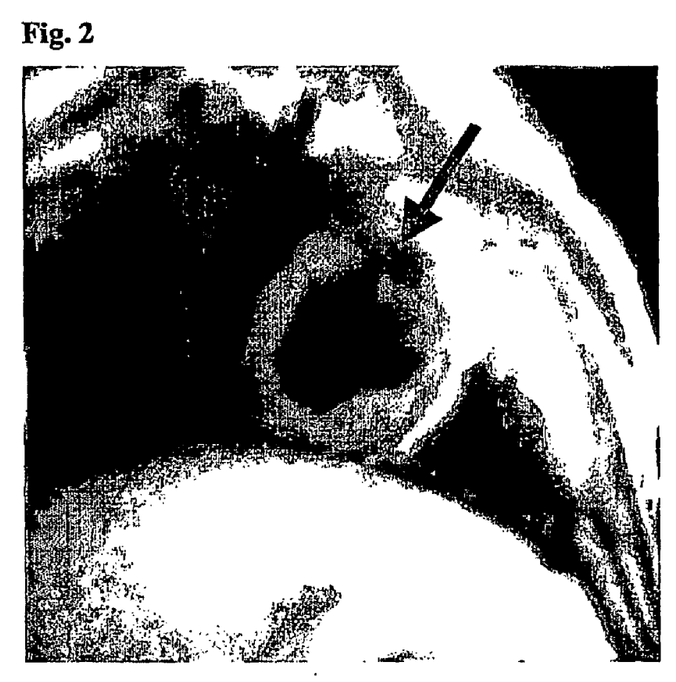
FIG. 2 is a short axis view image of an underperfused area of the myocardium acquired 45 minutes post injection.
Figure 3:
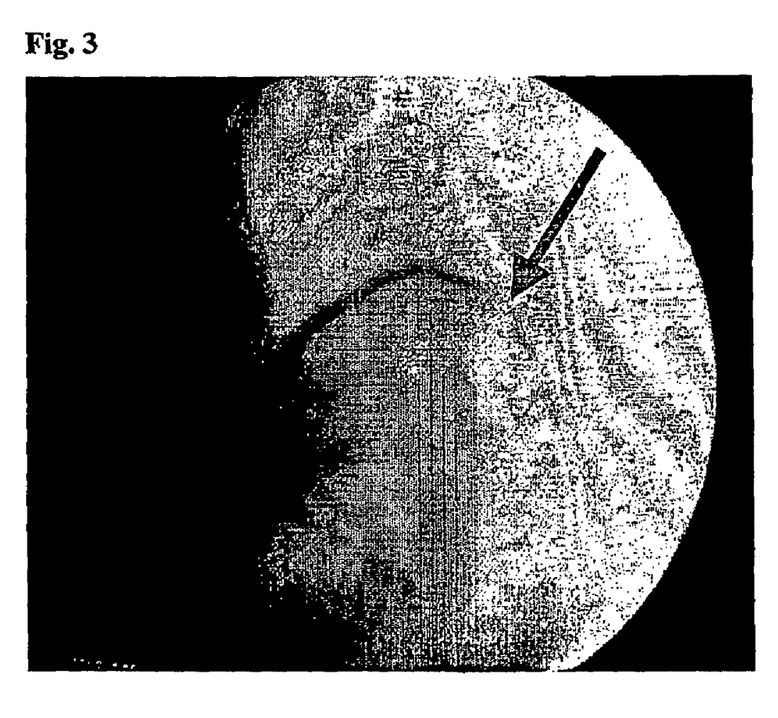
FIG. 3 is X-ray angiography image performed prior to and after a stress-test imaging experiment.

The pig was subjected to imaging at 1.5 T in a clinical scanner. Short axis view images of the myocardium were acquired 45 minutes post injection. The images visualised an underperfused area (see FIG. 2). X-ray angiography was performed prior to and after the stress-test imaging experiment (FIG. 3).

Example 5

Calculation of % Dissociation and Half-Life of MnHPTA and $Ca^{2+}$ Containing MnHPTA Preparations of MnHPTA containing 0, 0.5 and 1 equivalents of $Ca^{2+}$ by adding Ca-ascorbic acid to MnHPTA. The 200 mM manganese stock solutions of MnHPTA (with and without calcium) were diluted to 5 mM manganese by transferring 250 microliters of the stock solution into 10-ml of RO water.

10 ml of whole human blood was obtained from a healthy volunteer. The blood contained sodium heparin as the anticoagulant. The percent hematocrit of the blood was determined by micro-centrifugation techniques and the concentration of endogenous metal cations determined by ICP-AES.

Four 2 ml aliquots of the blood were prepared and warmed to 40° C. After warming, 40 microliters of 5 mM MnHPTA was added to the blood, resulting in sample with 0.1 mM manganese. The sample was inverted three times and the longitudinal relaxation time (T1) determined immediately. The T1 values were obtained using a 20 MHZ Bruker Minispec (Bruker Analytik GmbH, Rheinstetten, Germany) operating at 40° C. The T1 values were calculated from the mono-exponential fit of signal intensity versus time obtained from an inversion recovery sequence with 12 different inversion times. The T1 values were obtained every 5 minutes over a one hour time period. The above procedure was repeated for MnHPTA samples containing 0.5 and 1 equivalents of calcium.

The total percent dissociation of MnHPTA after one hour was determined form Equation 2. The complex half-lives were calculated (when possible) using a validated software program (Pharm-NCA version 1.4, InnaPhase, Champs-sur-Marne, France). The kinetic parameters were obtained using standard bi-exponential pharmacokinetic analysis, and the complex half-life was determined according to:

$$C(t) = f_a \exp\left(\frac{-0.693t}{t_{1/2}a}\right) + f_b \exp\left(\frac{-0.693t}{t_{1/2}b}\right)$$

where $t_{1/2}a$ and $t_{1/2}b$ are the complex half-time of the two components, and fa and fb represent the fractional volumes of the two compartments.

The results of the study indicate that more than 80% of the MnHPTA complex is dissociated within 1 minute after exposure to whole human blood. The addition of calcium did not alter the dissociation kinetics.

Example 7

Cardiovascular Effects of MnHPTA with Various Amounts of $Ca^{2+}$

The cardiovascular effects of MnHPTA with various amounts of $Ca^{2+}$ (0, 0.5 and 1 mol $Ca^{2+}$ per mol $Mn^{2+}$) were investigated in the presence and absence of dobutamine induced pharmacological stress in anaesthetised dogs.

Anaesthesia was induced with pentobarbital (12-25 mg/kg i.v.) and fentanyl (1.5-2.5 µg/kg i.v.), followed by a continuous i.v. infusion of fentanyl (20 µg/kg/h and pentobarbital (10 mg/kg/h). Artificial ventilation was carried out by room air through a tracheal tube, aimed at achieving normal physiological blood gas values. A catheter was introduced through the right femoral artery for measurement of SAP. A microtip pressure transducer catheter (Millar) was placed into the left ventricle through the carotid artery for measurements of LVdP/dt. A Swan-Ganz catheter was introduced through the right femoral vein for measuring PAP (pulmonary arterial pressure). A 3-lead ECG was continuously-monitored. An ultrasonic flow probe was placed around the left femoral artery for flow measurement. Venflon cannulas were introduced into the left and right jugular veins for contrast agent injections and dobutamine infusions, respectively.

Injections of MnHPTA (with various addition of $Ca^{2+}$) were performed as rapid bolus injections (injection of the whole dose of 30 µmol/kg over 10 seconds) via a peripheral forelimb vein. Saline was used as a control substance. All injections were first performed during dobutamine stress, followed by injection at rest, i.e. in the absence of dobutamine stress. Dobutamine infusion was performed at a dose of 5-20 µg/kg/min. The exact dose was be chosen by titration from the lowest dose until an increase in systolic arterial pressure by about 50% was observed. The dobutamine infusion was continued for 2 minutes after injection of MnHPTA followed by 3 min infusion at 30% of the chosen dose. The dobutamine infusion was thereafter terminated.

Systolic, diastolic and mean systemic arterial pressure (SYS, DIA MEAN), LVdP/dt, femoral arterial flow, mean PAP (pulmonary arterial pressure), HR (heart rate) and ECG were continuously monitored and stored by a computer system.

MnHPTA Injection During Dobutamine Stress:

Dobutamine alone increased most of the monitored haemodynamic parameters. The most pronounced increase was seen in dP/dt max that increased 4 times. Saline injection did not cause any major changes in the measured haemodynamic parameters. The haemodynamic effects seen upon injection of 30 µmol/kg MnHPTA peaked within 2 minutes, i.e., during maximal dobutamine infusion. The most pronounced increase in BR (about 50%) was seen after MnHPTA without $Ca^{2+}$, with a simultaneous increase in femoral blood flow. Addition of $Ca^{2+}$ attenuated these effects; 0.5 mol $Ca^{2+}$ per mol $Mn^{2+}$ to a somewhat larger extent than 1 mol $Ca^{2+}$ per mol $Mn^{2+}$. Although the other parameters were affected modestly, MnHPTA with 0.5 mol $Ca^{2+}$ per mol $Mn^{2+}$ was closer to the saline control in all instances compared to MnHPTA with 0 or 1 mol $Ca^{2+}$ per mol $Mn^{2+}$.

MnHPTA Injection During Rest:

Most parameters stayed close to the saline control after injection of MnHPTA. However, systemic blood pressure, in particular DIA was transiently lowered upon MnHPTA injection, independently on the $Ca^{2+}$ content. The dP/dt max increased upon increase in the $Ca^{2+}$ content of MnHPTA.

Example 8

Comparison of Uptake of MnHPTA Containing Various Amounts of $Ca^{2+}$

Comparison of uptake of MnHPTA containing 0, 1, 2 and 6 mol $Ca^{2+}$ per mol $Mn^{2+}$ was studied in a pig model by using quantitative assessment of the R1 change in pre and post injection.

12 pigs divided into 4 groups received MnHPTA in a dose of 15 µmol/kg body weight, the MnHPTA containing 0, 1, 2 and 6 mol $Ca^{2+}$ per mol $Mn^{2+}$. R1 was assessed using a Lock-Locker sequence with 70 data points following the signal recovery after an initial 180° inversion pulse in a short axis view of the myocardium. A monoexponential curve describing the T1 recovery was fitted to the data and compensation of the rf-excitations was performed. The R1 and ΔR1 in the myocardium was then calculated from the fitted T1 curves.

Higher amounts of $Ca^{2+}$ (2 and 6 mol $Ca^{2+}$ per mol $Mn^{2+}$) resulted in significantly lower ΔR1 at the early phase (0 to 20 min). This can be explained by the fact that the initial uptake of Mn into the myocardium is limited due to Ca competing with Mn for the uptake. However, at the late phase (30 to 60 min) contrast enhancement is similar regardless the amount of Ca.

What is claimed is:

1. A method of magnetic resonance (MR) imaging to identify diseased areas comprising areas suffering from myocardial ischemia, said method comprising
    a) administering to a human or non-human animal body a contrast agent comprising
        (i) at least one complex of the formula $Mn_m$ HPTA $Z_o$, wherein m is 1 or 2, o is 0 to 2, Z is hydrogen or a pharmaceutical acceptable counterion, HPTA is 1,7-dicarboxy-2,6-bis(carboxymethyl)-4-hydroxy-2,6-diaza)-heptane,
        wherein said complex has a thermodynamic formation constant between $10^3$ and $10^{16}$ and wherein said complex shows a dissociation of greater than 50% and a half-life of less than 1 minute under physiological conditions; and
        (ii) 0 to 2 mol $Ca^{2+}$ per mol $Mn^{2+}$;
    b) exposing said body to a regime of physical and/or pharmacological stress before or simultaneously to the contrast agent administration;
    c) collecting MR imaging data and;
    d) providing MR images of an area of interest; and identifying the areas suffering from myocardial ischemia using the MR images.

2. The method according to claim 1, wherein the contrast agent comprises a mixture said complex.

3. The method according to claim 1, wherein the thermodynamic formation constant k is between $10^5$ and $10^{10}$.

4. The method according to claim 1, wherein the contrast agent comprises 0.1 to 1.75 mol $Ca^{2+}$ per mol $Mn^{2+}$.

5. The method according to claim 1, wherein the contrast agent comprises 0.5 to 1 mol $Ca^{2+}$ per mol $Mn^{2+}$.

6. The method according to claim 1 where Mn is $Mn^{2+}$, o is 0 or 2 and Z is hydrogen, sodium or calcium.

7. The method according to claim 1, wherein the stress is a physical stress.

8. The method according to claim 1, wherein the contrast agent is administered at peak stress.

9. The method according to claim 3, wherein the thermodynamic formation constant k is between $10^7$ and $10^{9.5}$.

10. The method according to claim 1, wherein the area of interest is the myocardium.

11. A mixture comprising a complex having a thermodynamic formation constant between $10^3$ and $10^{16}$ which comprises $Mn^{2+}$ and a complexing moiety, wherein said complexing moiety is HPTA and said complex shows a dissociation of greater than 50% and a half-life of less than 1 minute under physiologic conditions and 0.1 to 2 mol $Ca^{2+}$ per mol $Mn^{2+}$ for the manufacture of a contrast agent for use in MR imaging of the myocardium.

12. The mixture according to claim 11, wherein the mixture comprises 0.5 to 1 mol $Ca^{2+}$ per mol $Mn^{2+}$.

13. Mixture for use in the MR imaging detection of myocardial ischemia and infarction wherein said mixture comprises
    (i) at least one complex of the formula $Mn_m$HPTA $Z_o$, wherein m is 1 or 2, o is 0 to 2, Z is hydrogen or a pharmaceutical acceptable counterion,
    wherein said complex has a thermodynamic formation constant between $10^3$ and $10^{16}$ and wherein said complex shows a dissociation of greater than 50% and a half-life of less than 1 min under physiological conditions; and
    (ii) 0 to 2 mol $Ca^{2+}$ per mol $Mn^{2+}$.

* * * * *